United States Patent
Johnson et al.

(10) Patent No.: US 9,486,822 B2
(45) Date of Patent: *Nov. 8, 2016

(54) DEVICES FOR IMPROVED DELIVERY OF VOLATILE LIQUIDS

(75) Inventors: Andrew Johnson, Hull (GB); Loic Marouse, Hull (GB)

(73) Assignee: Reckitt & Colman (Overseas) Limited, Slough, Berkshire (GB)

( * ) Notice: Subject to any disclaimer, the term of this patent is extended or adjusted under 35 U.S.C. 154(b) by 36 days.

This patent is subject to a terminal disclaimer.

(21) Appl. No.: 14/128,090

(22) PCT Filed: Jun. 21, 2012

(86) PCT No.: PCT/GB2012/051442
§ 371 (c)(1),
(2), (4) Date: Feb. 25, 2014

(87) PCT Pub. No.: WO2012/175972
PCT Pub. Date: Dec. 27, 2012

(65) Prior Publication Data
US 2014/0166781 A1    Jun. 19, 2014

(30) Foreign Application Priority Data

Jun. 24, 2011   (GB) .................................. 1110738.0

(51) Int. Cl.
*A61M 11/06* (2006.01)
*B05B 7/24* (2006.01)
(Continued)

(52) U.S. Cl.
CPC ............... *B05B 7/24* (2013.01); *A01M 1/205* (2013.01); *A01M 1/2044* (2013.01); *A61L 9/127* (2013.01);
(Continued)

(58) Field of Classification Search
CPC .................. A61L 2209/135; A61L 2209/133; A61M 11/06; A61M 11/02; A01M 1/2044
USPC ......................................................... 239/326
See application file for complete search history.

(56) References Cited

U.S. PATENT DOCUMENTS 2,612,432 A * 9/1952 Boddy ................ A01M 1/2077
392/390
2,814,081 A * 11/1957 Stevenson ................ A47K 7/04
422/105

(Continued)

FOREIGN PATENT DOCUMENTS

EP          0092359 A3      4/1983
EP          1076014 A3      2/2001
(Continued)

OTHER PUBLICATIONS

International Search Report for PCT/GB2012/051442 dated Oct. 17, 2012.
(Continued)

*Primary Examiner* — Arthur O Hall
*Assistant Examiner* — Chee-Chong Lee
(74) *Attorney, Agent, or Firm* — Norris McLaughlin & Marcus PA

(57) ABSTRACT

An emanation system is described comprising and emanation device and a replaceable refill of liquid, wherein the refill comprises: a sealed reservoir of a liquid containing one or more active materials wherein the active material comprises at least one of: a fragrance; an insecticide; a fungicide; a pesticide; a sanitizing material; and/or a pharmaceutical; a porous wick having a length which extends from the interior of the reservoir to the exterior thereof; a reservoir seal having at least one aperture through which the porous wick extends; and a hollow liquid conduit housed within the wick having a length substantially identical to the wick; and wherein the device comprises: an air pump; a fluid conduit in fluid communication with the air pump such that, in use, air pumped by the pump will flow through the fluid conduit; a nozzle located at the end of the fluid conduit remote from the air pump; a ejector constriction provided in the fluid conduit adjacent or substantially adjacent the nozzle; a liquid conduit engaging member provided adjacent the ejector constriction and in fluid communication with the fluid conduit at one end thereof, and configured at the other end to, in use, engage the hollow liquid conduit in the refill; characterized in that a mechanism is provided to permit the liquid conduit engagement member to form a liquid tight seal with the liquid conduit.

12 Claims, 3 Drawing Sheets

(51) Int. Cl.
*A61L 9/12* (2006.01)
*A61L 9/14* (2006.01)
*A01M 1/20* (2006.01)
*A61M 11/02* (2006.01)

(52) U.S. Cl.
CPC ............... *A61L 9/14* (2013.01); *B05B 7/2416* (2013.01); *B05B 7/2459* (2013.01); *A61L 2209/133* (2013.01); *A61L 2209/135* (2013.01); *A61M 11/02* (2013.01); *A61M 11/06* (2013.01)

(56) References Cited

U.S. PATENT DOCUMENTS

| | | | |
|---|---|---|---|
| 3,796,541 A * | 3/1974 | Gentil | A61L 2/204 137/454 |
| 3,872,280 A * | 3/1975 | Van Dalen | A61L 9/03 128/203.27 |
| 4,166,087 A * | 8/1979 | Cline | A61L 9/122 239/56 |
| 4,200,229 A | 4/1980 | Spector | |
| 4,346,059 A | 8/1982 | Spector | |
| 4,370,300 A * | 1/1983 | Mori | A61L 2/24 261/102 |
| 4,950,457 A * | 8/1990 | Weick | B60H 3/0007 239/59 |
| 2002/0130146 A1 | 9/2002 | Borut et al. | |
| 2002/0168301 A1 | 11/2002 | Channer | |
| 2005/0178345 A1 | 8/2005 | Crapser | |
| 2005/0199742 A1 | 9/2005 | Maat | |
| 2006/0022064 A1 | 2/2006 | Triplett et al. | |
| 2006/0045359 A1 | 3/2006 | Chen et al. | |
| 2006/0175425 A1 | 8/2006 | McGee et al. | |
| 2007/0204387 A1 | 9/2007 | Cornelius et al. | |
| 2007/0217771 A1* | 9/2007 | Granger | A01M 1/2033 392/386 |
| 2008/0149665 A1 | 6/2008 | Hafer et al. | |
| 2008/0251598 A1 | 10/2008 | Ross | |
| 2010/0187324 A1 | 7/2010 | Feygin et al. | |
| 2010/0243754 A1 | 9/2010 | Harris | |

FOREIGN PATENT DOCUMENTS

| | | |
|---|---|---|
| EP | 1714662 A1 | 10/2006 |
| EP | 1849485 A1 | 10/2007 |
| FR | 2556242 A1 | 6/1985 |
| GB | 2233230 A | 1/1991 |
| GB | 2357973 A | 7/2001 |
| GB | 2480906 A | 12/2011 |
| GB | 2481635 A | 1/2012 |
| WO | 9607484 A1 | 3/1996 |
| WO | 9949904 A1 | 10/1999 |
| WO | 03003826 A3 | 1/2003 |
| WO | 03103387 A3 | 12/2003 |
| WO | 2004002542 A1 | 1/2004 |
| WO | 2004094071 A1 | 11/2004 |
| WO | 2004096299 A1 | 11/2004 |
| WO | 2006004891 A1 | 1/2006 |
| WO | 2006045359 A1 | 5/2006 |
| WO | 2007109504 A3 | 9/2007 |
| WO | 2008034977 A3 | 3/2008 |
| WO | 2011098641 A1 | 8/2011 |
| WO | 2011161462 A1 | 12/2011 |
| WO | 2012001404 A1 | 1/2012 |
| WO | 2012001405 A1 | 1/2012 |
| WO | 2012059771 A1 | 5/2012 |

OTHER PUBLICATIONS

International Preliminary Report on Patentability for PCT/GB2012/051442 dated Dec. 24, 2013.
Written Opinion of the International Searching Authority for PCT/GB2012/051442 dated Oct. 17, 2012.

* cited by examiner

DEVICES FOR IMPROVED DELIVERY OF VOLATILE LIQUIDS

This is an application filed under 35 USC 371 of PCT/GB2012/051442.

FIELD OF THE INVENTION

The present invention relates to devices and methods for improved airborne delivery of volatile liquids containing one or more active materials wherein the active material comprises at least one of: a fragrance; an insecticide; a fungicide; a pesticide; a sanitising material; and/or a pharmaceutical.

BACKGROUND

Volatile liquids containing one or more active materials wherein the active material comprises at least one of: a fragrance; an insecticide; a fungicide; a pesticide; a sanitising material; and/or a pharmaceutical are delivered within the domestic environment via a variety of mechanisms. Devices are available with heaters disposed therein to increase the rate of emanation from a surface saturated with the liquid, such a surface could be a wick saturated with a fragranced liquid and the heater is located adjacent the wick surface and nearby a chimney to heat the liquid on the wick surface and cause it to more readily evaporate and disseminate into the surrounding environment through the chimney.

Alternatively such volatile liquids can be loaded in an aerosol canister, the canister holds the liquid under pressure and when the canister valve is opened the liquid is forced out. The liquid is provided with a propellant which evaporates inside the canister to maintain an even pressure and, outside the canister, assist with the mechanical break up of the liquid by evaporating rapidly. Suitable propellants include volatile hydrocarbons such as propane, butane or isobutane.

Aerosols generally provide a satisfactory spray performance but since they require manual operation by a user, they are not considered to be particularly convenient for routine use. Automatic aerosol activation devices exist for operation with metered dose aerosols. These devices are operable to periodically actuate the aerosol to cause a dose of the liquid to be sprayed.

Whilst the automation of the device overcomes the problem of manual operation of a canister, the use of aerosols containing such propellants is becoming increasingly less desirable since these volatile hydrocarbons carry the disadvantage of being flammable, the rising cost of oil is rendering them increasingly expensive and they also carry the further disadvantage of being an atmospheric source of carbon which is deemed to not be environmentally sensitive.

In the field of air freshening it is generally preferred to use a fragranced volatile liquid/air freshening liquids comprising several components. These components often possess different volatilities which can lead to emission problems. The effect of fractionation can be particularly pronounced for powered emanation devices using a heater to effect emanation such as a plug-in emanation device or the like.

In such device a build-up phenomenon can occur in which an accumulation of volatile liquid components with the lowest comparative volatilities can occur leading to an undesirable non-uniform emanation profile for the liquid. This phenomenon can produce an olfactory sensation wherein the fragrance character changes over the course of emanation of a quantity of the fragranced volatile liquid such that the 'high notes' of a fragrance are the first to be evaporated when the wicking material is first exposed to the fragranced liquid, and the 'low notes' are evaporated thereafter.

Accordingly, it is an object of the present invention to provide a device that is capable of addressing the above-mentioned performance drawbacks and other drawbacks that will be appreciated by a person skilled in the art.

SUMMARY OF INVENTION

According to a first aspect of the present invention there is provided therefore an emanation system comprising and emanation device and a replaceable refill of liquid, wherein the refill comprises:

a sealed reservoir of a liquid containing one or more active materials wherein the active material comprises at least one of: a fragrance; an insecticide; a fungicide; a pesticide; a sanitising material; and/or a pharmaceutical;

a porous wick having a length which extends from the interior of the reservoir to the exterior thereof;

a reservoir seal having at least one aperture through which the porous wick extends; and a hollow liquid conduit housed within the wick having a length substantially identical to the wick;

and wherein the device comprises:

an air pump;

a fluid conduit in fluid communication with the air pump such that, in use, air pumped by the pump will flow through the fluid conduit;

a nozzle located at the end of the fluid conduit remote from the air pump;

a ejector constriction provided in the fluid conduit adjacent or substantially adjacent the nozzle;

a liquid conduit engaging member provided adjacent the ejector constriction and in fluid communication with the fluid conduit at one end thereof, and configured at the other end to, in use, engage the hollow liquid conduit in the refill;

characterised in that a mechanism is provided to permit the liquid conduit engagement member to form a liquid tight seal with the liquid conduit.

According to a second aspect of the present invention there is provided therefore an emanation system comprising and emanation device and a replaceable refill of liquid, wherein the refill comprises:

a sealed reservoir of a liquid containing one or more active materials wherein the active material comprises at least one of: a fragrance; an insecticide; a fungicide; a pesticide; a sanitising material; and/or a pharmaceutical;

a porous wick having a length which extends from the interior of the reservoir to the exterior thereof;

a reservoir seal having at least two apertures, wherein the wick extends through one of the apertures; and a hollow liquid conduit which extends from the interior of the reservoir to engage with one of the apertures;

and wherein the device comprises:

an air pump;

a fluid conduit in fluid communication with the air pump such that, in use, air pumped by the pump will flow through the fluid conduit;

a nozzle located at the end of the fluid conduit remote from the air pump;

a ejector constriction provided in the fluid conduit adjacent or substantially adjacent the nozzle;

a liquid conduit engaging member provided adjacent the ejector constriction and in fluid communication with the fluid conduit at one end thereof, and configured at the other end to, in use, engage the hollow liquid conduit in the refill; characterised in that a mechanism is provided to permit the liquid conduit engagement member to form a liquid tight seal with the liquid conduit.

Devices according to either the first of second aspect of the present invention have been found to be particularly advantageous as they are capable of spraying the volatile liquid at a uniform consistency thus avoiding the drawbacks of fractionation and/or build-up phenomena.

The mechanism is preferably arranged to permit the liquid conduit engagement member to move in a generally downward direction toward an open end of the liquid conduit when the refill is loaded in the device.

Alternatively the mechanism may be arranged to permit refill securing means to move in a generally upward direction toward the liquid conduit engagement member to engage with the liquid conduit when a refill is loaded in the device.

As a further alternative the mechanism may be arranged to permit refill securing means to move in a generally upward direction toward the liquid conduit engagement member and substantially simultaneously therewith the mechanism also permits the liquid conduit engagement member to move in a generally downward direction toward the refill, such dual movement permitting the liquid conduit engagement member to engage with the liquid conduit when a refill is loaded in the device.

Preferably the end of the liquid conduit engagement member is inwardly tapered and/or the open end of the liquid conduit is outwardly tapered to permit an ease of engagement therebetween.

Preferably the mechanism is motorised and can be activated by a user input to the device to instruct the mechanism to cause the liquid conduit engagement member to engage with the liquid conduit and vice versa.

Alternatively or additionally the mechanism may be operated by a user moving components of the device to cause the liquid conduit engagement member to engage with the liquid conduit and vice versa.

The liquid conduit is preferably made from a rigid or substantially rigid material such as a metal, alloy or plastics material, this may be advantageous in allowing said conduit to penetrate the wick.

The hollow liquid conduit in the first aspect of the present invention is provided with length that is substantially identical to the length of the wick, this is advantageous as it permits the manufacture of the wick and conduit to be less expensive as it can be manufactured together and/or cut into desired lengths together.

The hollow liquid conduit in the second aspect of the present invention is preferably provided with length that permits it to extend between the extremity of the reservoir remote to the seal and the seal with the conduit preferably terminating at or adjacent the seal.

The refill may be made from a reservoir that is partially or completely transparent thus allowing a user to monitor the liquid level therein. Preferably the reservoir is made from glass or a substantially rigid plastics material.

The reservoir seal is preferably sized to correspond to the diameter or cross-section of the wick thus securely holding the wick in a fixed position whilst substantially maintaining a liquid seal to substantially or completely prevent the leaking of liquid from the reservoir.

The refill is preferably provided with a removable cap that surrounds the plug and the protruding wick to protect the wick and prevent emanation of the volatile liquid from the wick until emanation of the volatile liquid is required.

The wick is preferably made from a wrapped fibrous material, such as wrapped cellulose or the like. The wick may be made from any porous material wherein said porous material sufficiently malleable to permit the liquid conduit to be at least partially inserted therein.

The wick is preferably sized to extend from a base of reservoir to protrude through the plug or a reservoir seal to extend thereabove.

A further advantage of the present invention over typical devices used for emanating volatile liquids from a wicked replaceable refill, such as a mains electrical plug in diffuser, is that since heat is not used to drive the emanation of the volatile liquid, there will be no unsightly discolouration of the wick.

The securing means may comprise a platform that supports a base surface of the refill when loaded in the device. Alternatively or additionally the securing means may releasably grip an upper portion of the refill, preferably a neck portion of the refill, when the refill is loaded in the device.

The air pump is preferably configured to pump air through the fluid conduit within a range of substantially 0.4-1.0 liters/min, and preferably substantially 0.6-0.8 liters/min.

The ejector constriction is preferably provided in the form of a nozzle insert, even more preferably said nozzle insert substantially fills the nozzle and permits the flow of volatile liquid therefrom.

The nozzle insert is preferably configured to extend from or adjacent the nozzle along the interior of the fluid conduit and may be provided at a rearward portion thereof that is remote from the nozzle with a channel. The channel may be inwardly tapered toward a forward portion thereof to, in use, further lower the pressure and increase the speed of air pumped therethrough, forward of the inward taper may be provided a ejector constriction portion. Forward from said ejector constriction portion may be provided an expansion chamber. The liquid conduit engaging member preferably connects to the fluid conduit in the ejector constriction portion to be in fluid communication with the fluid conduit and/or the nozzle insert such that, in use, the decrease in pressure at the connection draws liquid up the liquid conduit n the refill into the liquid conduit engaging member and into the fluid conduit and/or nozzle insert before being carried by the pumped air flow out of the nozzle or nozzle insert into the environment surrounding the device.

Alternatively the ejector constriction can be formed integrally with the fluid conduit adjacent the nozzle. As a further alternative the ejector constriction can be formed integrally with the nozzle.

The nozzle or nozzle insert may be provided with one or more break-up bars and/or swirl chambers in order to improve the mechanical break up of the volatile liquid being sprayed therefrom in use.

The device is preferably provided with a controller that is configured to control the air pump to control the spraying of volatile liquid from the device. Preferably the controller is provided with a timer to permit the controller to instruct the pump to operate for periods defined by the controller. The device may be provided with user input means to allow a user to instruct the controller how long to spray for and/or how often to spray for and/or the spray rate of the device.

The device may be provided with a sensor means which is connected to the controller wherein said sensor means is configured to detect a characteristic in the environment surrounding the device. The controller would preferably be operative to analyse an input from the sensor means and control the air pump to spray a determined amount of volatile liquid.

Preferably the sensor means is provided by at least one motion sensor means and/or at least one odour sensor means.

The motion sensor means may be provided in the form of at least one of: an infrared (IR) sensor; a laser sensor; and a sound sensor. The IR sensor, which is preferably a passive IR sensor, may be operable to detect radiation in the infrared spectrum, thus be capable of detecting the presence of a person or an animal within the vicinity of the device. The laser sensor may be operable to emit one or more laser beams and be adapted to detect when an object breaks the one or more beams by moving across the beam(s), thus indicating the presence of a person or an animal within the vicinity of the device. The sound sensor may be operable to detect sound within the vicinity of the device and, preferably, once the detected sound exceeds a predefined level this is indicative of movement within the vicinity of the device.

The odour sensor means may be provided by a MOS sensor or the like and may be operable to detect common household odours (and the chemicals which constitute) these malodours. For example: kitchen malodour; bathroom malodour; tobacco smoke; pet odours; mould and/or mildew; body odour; fish; onions; garbage; fragrance from other products (such as detergents, polishes, cleaning products etc). To facilitate such detection the odour sensor means may be operable to detect at least some of the following chemical components: amines and nitrogen compounds; acids and/or sulphur compounds, such as mercaptans, thioacids, thioesters, sulfides, phenols and skatole.

The device of any of the above-mentioned aspects may be provided with an indicator wherein said indicator is operable to indicate to a user what function the device is currently performing. The indicator may be operable to provide a visual indication and/or provide an audible indication.

Preferably the indicator is configured to provide a visual indication by emitting light from one or more light sources, preferably one or more LEDs.

The one or more light sources may be adapted to emit a different colour of light to indicate the current function the device is performing. Additionally or alternatively, the one or more light sources may blink or flash to indicate the current function the device is performing.

Alternatively or additionally, the device may be operable to visually indicate the function currently being performed by the device via a screen. The screen may be an LCD screen that is adapted to provide a message to a user, for instance such messages could include "ON", "DISPENSING", "RESTING", "NORMAL MODE", "DETECTING MODE", "BOOST MODE", "OFF".

The device may be power by mains-supplied electricity and/or be battery powered and/or be powered by solar cells located on the device. Most preferably the device is battery powered however to improve the portability thereof. Indeed battery powered is preferred as the use of such power is consider to be particularly advantageous over typical devices used for emanating volatile liquids from a wicked replaceable refill, such as a mains electrical plug in diffuser, is that the device does not need to be located adjacent an electrical plug socket nor within an acceptable distance of the socket such that there can be a electrical power cord between the device and plug socket, thus providing true portability.

Any of the features described herein may be combined with any of the above aspects in any combination.

DESCRIPTION OF AN EMBODIMENT

Figure 1:
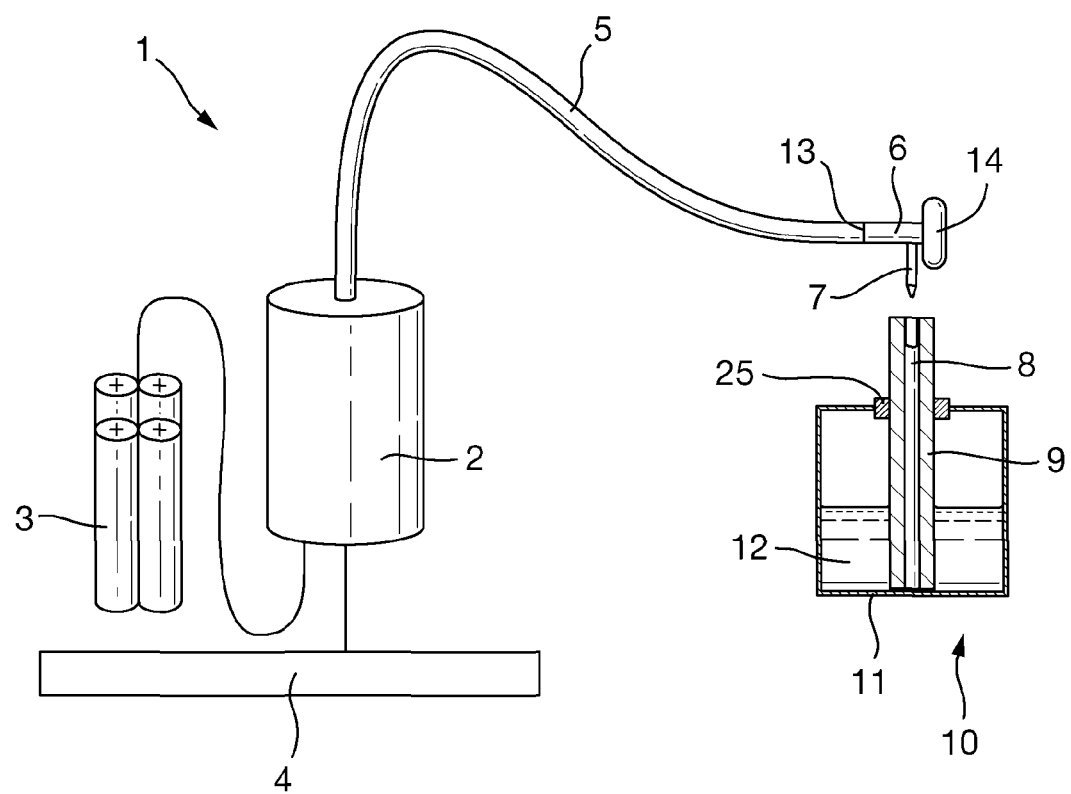
FIG. 1 illustrates an exploded view of the principle components of a system according to the first aspect of the present invention.

FIG. 1 illustrates an exploded view of the principle components of the system according to the first aspect of the present invention. The device 1 consists of an air pump 2 which is powered by batteries 3 and controlled by a controller 4 provided in the form of a PCB with suitable components attached thereto to facilitate control of the air pump 2.

The air pump 2 is shown in fluid communication with a fluid conduit 5 such that air pumped by the pump 5 is pumped into the fluid conduit 6. The pumped air passes along the fluid conduit through a nozzle insert 6 (discussed in greater detail below) and out of a nozzle (not shown). Connected to the fluid conduit 5 around the nozzle insert 6 is a liquid conduit engaging member 7.

The liquid conduit engaging member 7 is made from a rigid or substantially rigid material such as a metal, alloy or plastics material, and is of a generally tubular construction to permit volatile liquid to be transported therein and having a generally tapered end to permit engagement with a hollow liquid conduit 8.

The refill 10 comprises a reservoir 11 that is partially or completely transparent thus allowing a user to monitor the volatile liquid 12 level therein. The reservoir 11 is sealed with a seal 25 having an aperture therethrough, and the aperture is sized to correspond to the diameter or cross-section of the wick 9 to securely hold it in a fixed position whilst substantially maintaining a liquid seal to substantially or completely prevent the leaking of liquid from the reservoir.

Although not shown in detail in FIG. 1, the nozzle insert 6 is configured to be held in place by the nozzle and extend therefrom along the interior of the fluid conduit 5. At a rearward portion 13 of the nozzle insert 6 a channel is provided which may be inwardly tapered toward a forward portion (i.e. toward the nozzle) thereof to, in use, further lower the pressure and increase the speed of air pumped therethrough. Forward of the inward taper may be provided a ejector constriction portion 14 and forward from said ejector constriction portion may be provided an expansion chamber. The liquid conduit 8 connects to the fluid conduit 5 in the ejector constriction 14 portion to be in fluid communication with the fluid conduit 5 and/or the nozzle insert 6 such that, in use, the decrease in pressure at the connection draws liquid up the liquid conduit 8 into the liquid conduit engaging member 7 and further into the fluid conduit 5 and/or nozzle insert 6 before being carried by the pumped air flow out of the nozzle into the environment surrounding the device 1.

Figure 2:
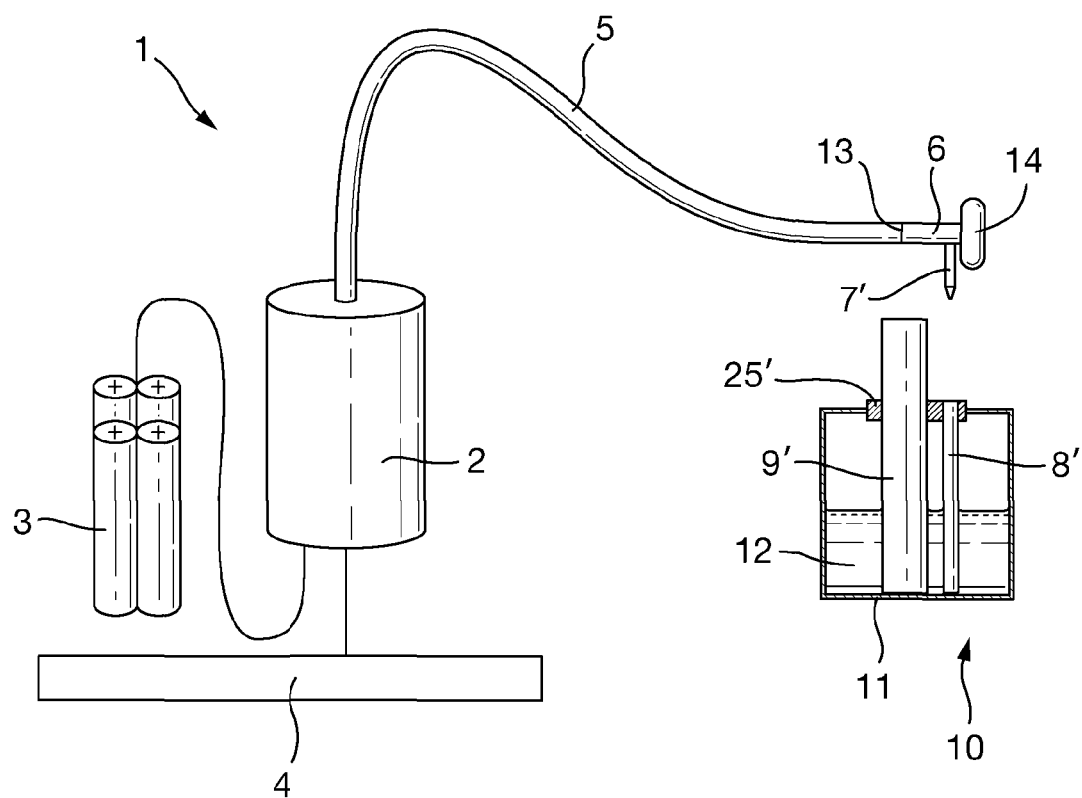
FIG. 2 illustrates an exploded view of the principle components of a system according to the first aspect of the present invention.

FIG. 2 illustrates an exploded view of the principle components of the system according to the second aspect of the present invention. The only difference of note over the system as described with reference to FIG. 1 is that the liquid conduit 7' is held by the seal 25' in a first aperture engagement with the liquid in the reservoir whereas the seal 25' holds the wick 9 in a second aperture. Additionally it can be seen that the conduit 7' terminates adjacent to a top surface of the seal 25' rather than a top surface of the wick 9'.

Figure 3:
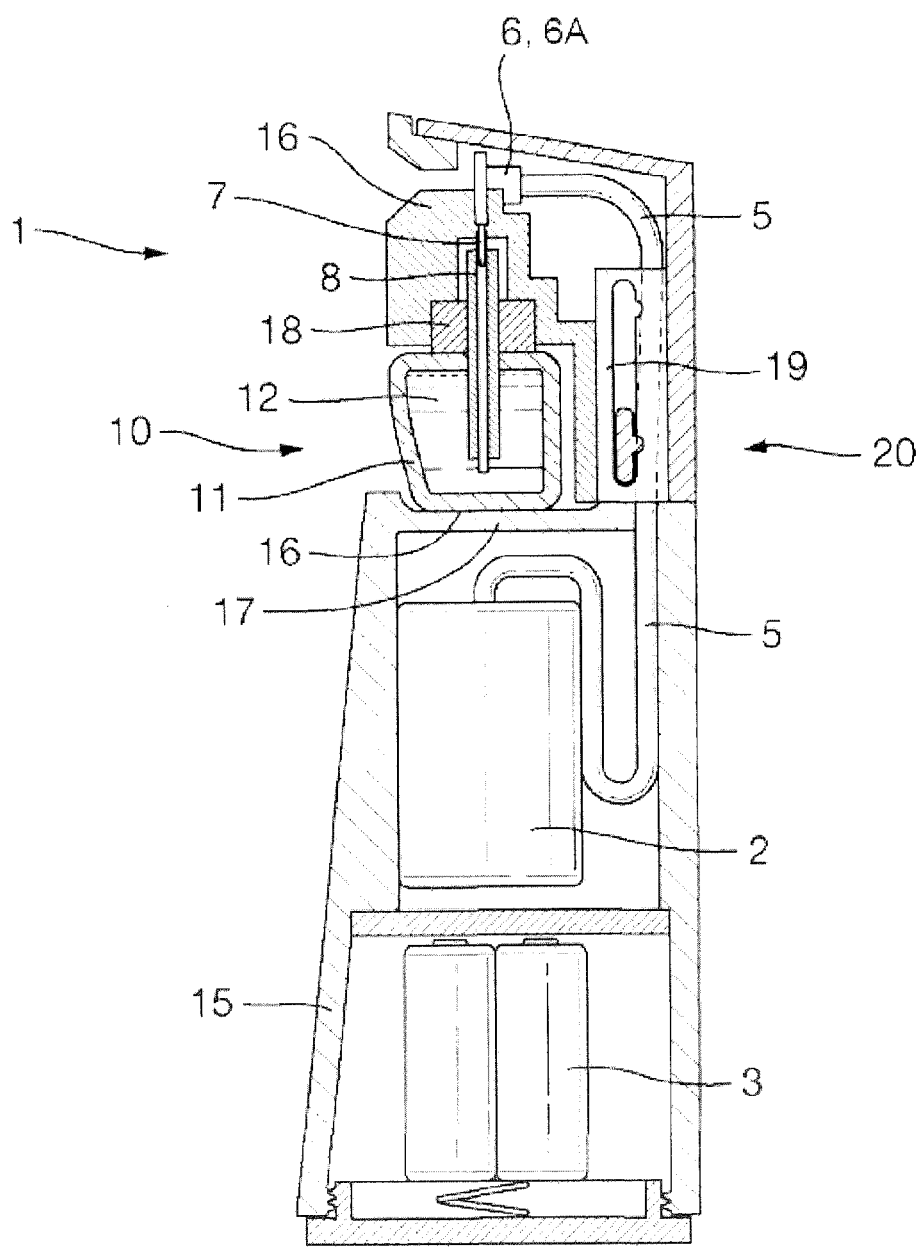
FIG. 3 illustrates a side sectioned view of a system according to the first aspect of the present invention.

Turning to FIG. 3 the device 1 is provided with a housing 15 which compartmentalises the components of the device, the batteries 3 are located within a base of the housing 15. Above the batteries 3 is located the air pump 2 and the fluid conduit 5 is connected thereto. A nozzle insert 6 and nozzle 6A are also shown. A securing means 16 is provided in the form of a platform 17 on which the refill 10 sits and also in the form of a neck gripping means 18 which is arranged to grip an upper portion of the refill 10.

The mechanism is provided in the form of guide means 19 which permit an upper part 20 of the housing 15 to move away from the platform 17 in a generally upward direction defined by the guide means 19 to permit the refill 10 to be placed on the platform 17. Once the refill 10 is on the platform 15, the upper part 20 of the housing can be moved generally downwardly as defined by the guide means 19 to allow the liquid conduit engagement member 7 to penetrate the hollow liquid conduit 8 in the wick 9 of the refill. The neck gripping means 18 impinge on an upper portion of the refill 10 to prevent further ingress of the liquid conduit engagement member 7 into the liquid conduit to prevent damage from forcible insertion.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An emanation system comprising an emanation device and a replaceable refill of liquid,
wherein the refill comprises:
a sealed reservoir of a liquid containing one or more active materials which comprises at least one of: a fragrance; an insecticide; a fungicide; a pesticide; a sanitising material; and/or a pharmaceutical;
a porous wick having a length which extends from an interior of the reservoir to an exterior thereof;
a hollow liquid conduit housed within the wick having a length substantially identical to the wick; and,
a reservoir seal having at least one aperture through which the porous wick extends and which forms a liquid seal between the reservoir seal and the porous wick;
and wherein the device comprises:
an air pump adapted to pump air through a fluid conduit which is in fluid communication with the air pump
a nozzle located at an end of the fluid conduit remote from the air pump;
an ejector constriction provided in the fluid conduit adjacent or substantially adjacent the nozzle, wherein the ejector constriction is a nozzle insert which is configured to extend from the nozzle or is adjacent to the nozzle and is present along the interior of the fluid conduit and is present at a rearward portion of the nozzle which is remote from the nozzle and which comprises a channel which is inwardly tapered toward a forward portion and an ejector constriction portion which extends from the inwardly tapered channel, and an expansion chamber which extends form the ejector constriction portion;
a liquid conduit engaging member connects to the fluid conduit in the ejector constriction portion and in fluid communication with the fluid conduit and/or the nozzle insert and which is adapted at the other end thereof to engage the hollow liquid conduit within the wick such that, during operation of the air pump, flowing air passing through the ejector constriction portion causes liquid present in the refill to be drawn therefrom via the hollow liquid conduit in the refill, into the liquid conduit engaging member and into the fluid conduit and/or nozzle insert before being forced by the pumped air flow out of the nozzle or nozzle insert and thereafter into the environment surrounding the device; and,
a mechanism which is adapted to permit the liquid conduit engagement member to form a liquid tight seal with the liquid conduit, wherein the mechanism is adapted to cause a refill securing means to move in a generally upward direction toward the liquid conduit engagement member and, substantially simultaneously therewith, the mechanism is also adapted to cause the liquid conduit engagement member to move in a generally downward direction toward the refill, such dual movement adapted to cause the liquid conduit engagement member to engage with the liquid conduit when a refill is loaded in the device.

2. An emanation system according to claim 1, wherein the end of the liquid conduit engagement member which is adapted to engage the hollow liquid conduit is inwardly tapered.

3. An emanation system according to claim 1, wherein the mechanism is motorised and can be activated by a user input to the device so to cause the mechanism to cause the liquid conduit engagement member to engage with the hollow liquid conduit housed within the wick.

4. An emanation system according to claim 1, wherein the mechanism is manually operable by a user in order to cause the liquid conduit engagement member to engage with the hollow liquid conduit housed within the wick.

5. An emanation system according to claim 1, wherein the hollow liquid conduit housed within the wick is made from a rigid or substantially rigid material.

6. An emanation system according to claim 1, wherein the hollow liquid conduit is of a length that permits it to extend between the extremity of the reservoir remote to the seal and the seal with the conduit, and preferably terminates at or adjacent the seal.

7. An emanation system according to claim 1, wherein a refill securing means comprises a platform which supports a base surface of the refill when the refill is loaded in the device.

8. An emanation system according to claim 1, wherein a refill securing means releasably grips an upper portion of the refill when the refill is loaded in the device.

9. An emanation system according to claim 1, wherein the air pump is adapted to pump air through the fluid conduit within a range of about 0.4-1.0 liters/min.

10. An emanation system according to claim 1, wherein the device is provided with a controller that is adapted to operate so to control the air pump and the spraying of volatile liquid from the device.

11. An emanation system according to claim 1, wherein an end of the hollow liquid conduit housed within the wick is outwardly tapered.

12. An emanation system according to claim 9, wherein the air pump is adapted to pump air through the fluid conduit within a range of about 0.6-0.8 liters/min.

\* \* \* \* \*